(12) United States Patent
Hamprecht et al.

(10) Patent No.: US 7,279,465 B2
(45) Date of Patent: Oct. 9, 2007

(54) USE OF AMPHIPHILIC NUCLEOSIDE PHOSPHONOFORMIC ACID DERIVATIVES FOR THE TREATMENT OF VIRAL INFECTIOUS DISEASES

(75) Inventors: Klaus Hamprecht, Tuebingen (DE); Gerhard Jahn, Rottenburg (DE); Herbert Schott, Tuebingen (DE)

(73) Assignee: Eberhard-Karls-Universitaet, Tuebingen (DE)

( * ) Notice: Subject to any disclaimer, the term of this patent is extended or adjusted under 35 U.S.C. 154(b) by 155 days.

(21) Appl. No.: 11/015,209

(22) Filed: Dec. 16, 2004

(65) Prior Publication Data

US 2005/0187183 A1    Aug. 25, 2005

Related U.S. Application Data

(63) Continuation of application No. PCT/EP03/06012, filed on Jun. 7, 2003.

(30) Foreign Application Priority Data

Jun. 19, 2002  (DE) ................. 102 28 059

(51) Int. Cl.
*A01N 43/04* (2006.01)
*A61K 31/70* (2006.01)
*C07H 19/00* (2006.01)
*C07H 21/00* (2006.01)

(52) U.S. Cl. .............. 514/49; 514/42; 514/43; 514/45; 514/50; 514/52

(58) Field of Classification Search ............ 514/42, 514/43, 45, 49, 50, 52
See application file for complete search history.

(56) References Cited

U.S. PATENT DOCUMENTS 5,679,652 A    10/1997  Schott
6,787,525 B1 *  9/2004  Schott et al. ............. 514/45

FOREIGN PATENT DOCUMENTS

| DE | 42 24 878 A1 | 2/1994 |
| WO | WO-98/38202 | 9/1998 |
| WO | WO-00/34298 | 6/2000 |

OTHER PUBLICATIONS

Crumpacker, New England J. of Medicine (1998) 335:721-731.
Eckle et al., Blood (2000) 96(9):3286-3289.
International Search Report for PCT/EP03/006012, mailed on Oct. 15, 2003, 3 pages.
Prix et al., Journal of Clinical Virology (1998) 11:29-37.
Prix et al., Journal of Infectious Diseases (1999) 180:491-495.

* cited by examiner

*Primary Examiner*—Patrick Lewis
(74) *Attorney, Agent, or Firm*—Morrison & Foerster LLP

(57) ABSTRACT

The invention relates to a method for treating infectious diseases which are elicited by viruses which are pathogenic to humans comprising the step of administering an amphiphilic nucleoside-phosphonoformic acid derivative having an esterified or unesterified carboxyl group, preferably of a nucleoside-glycerol-(hydroxycarbonyl)-phosphonate, as an active compound.

6 Claims, No Drawings

USE OF AMPHIPHILIC NUCLEOSIDE PHOSPHONOFORMIC ACID DERIVATIVES FOR THE TREATMENT OF VIRAL INFECTIOUS DISEASES

RELATED APPLICATION

This is a continuation application of International Patent Application PCT/EP 2003/006012, filed Jun. 7, 2003, designating the United States and published in German as WO 2004/000330, which claims priority to German Application Number 102 28 059.2, filed Jun. 19, 2002. The contents of the above-referenced applications are incorporated herein by this reference in their entireties.

BACKGROUND OF THE INVENTION

1. Field of the Invention

The invention relates to a method for treating viral infectious diseases comprising the step of administering an effective amount of amphiphilic nucleoside-phosphonoformic acid derivatives.

Viral infections, and diseases associated therewith, constitute complications which have to be taken seriously, particularly in the case of immunosuppressed patients. Immunosuppression for the purpose of avoiding rejection reactions is required, for example, in connection with transplanting solid organs and in connection with transplanting bone marrow or stem cells. Viral infectious diseases also constitute a particular risk, which has to be taken seriously, for patients who are suffering from immune diseases such as AIDS.

Developing antiviral pharmaceuticals has proved to be extremely difficult. This is due, in particular, to the fact that viruses only replicate in host cells and, in this connection, as intracellular parasites, use the enzymes of the host in addition to viral enzymes. Because of the complex interaction of the viral genome and the metabolism of the host cell, it is scarcely possible to stop virus replication without damaging the host cell. Furthermore, many viral infections only become clinically manifest when, as a consequence of the viral infestation, the host cells have already been irreversibly damaged.

In addition to human immunodeficiency virus (HIV), some members of the Herpesviridae family, in particular, play a prominent role in infectious diseases of immunosuppressed patients, inter alia. This group includes, for example, herpes simplex virus, varicella zoster virus (VZV), Epstein-Barr virus (EBV) and (human) cytomegalovirus (HCMV).

Like the other herpes viruses, human cytomegalovirus (HCMV) persists in the host throughout life after an infection. In immunocompetent individuals, human cytomegalovirus as a rule causes an infection picture which is similar to that of Pfeiffer's glandular fever. However, Heiniger at al. report that severe symptomatic HCMV infections, in the sense of an organ disease, can occur, for example, in patients who are undergoing surgical intensive care but who are not immunosuppressed. Only a fully functional immune system is able to prevent an HCMV disease in the wake of an HCMV infection.

2. Related Prior Art

Inhibitors of protein and nucleic acid synthesis can be used for chemotherapy purposes in connection with viral infections. A major problem in this regard is the toxicity which results from affecting the cellular mechanism as well.

At present, only three antiviral active substances which are approved for treating HCMV infections in humans are available: ganciclovir (GCV), foscarnet (sodium-phosphonoformic acid, PFA) and also cidofovir (CDV). Ganciclovir is an acyclic guanosine analogue and cidofovir is an acyclic deoxycytidine monophosphate (dCMP) analogue. As a salt of phosphonoformic acid, foscarnet differs markedly in its structure from these nucleoside/nucleotide analogues.

All three active compounds ultimately suppress viral DNA synthesis by inhibiting the HCMV DNA polymerase. As a prodrug, 9-[1,3-dihydroxy-2-propoxymethyl]guanine (ganciclovir) has first of all to be phosphorylated to ganciclovir triphosphate in order to express its antiviral activity. For this, it is phosphorylated to ganciclovir monophosphate by an HCMV-encoded phosphotransferase (UL97) in a first step. Host cell kinases then phosphorylate this monophosphate to the triphosphate by way of the diphosphate. During viral DNA synthesis, the ganciclovir triphosphate is incorporated, as a dGTP analogue, into the nascent strand, with this leading to chain termination of the DNA replication of the HCMV.

1-[(S)-3-Hydroxy-2-(phosphonomethoxy)propyl]cytosine dihydrate (cidofovir) is an acyclic nucleoside monophosphonate which has to be phosphorylated up to the triphosphate by cellular kinases in order to be converted into an active form. The phosphorylation is carried out by host enzymes and is consequently independent of virus-encoded kinases. As in the case of GCV triphosphate, incorporation of CDV triphosphate (CDV-TP) into the newly forming viral DNA strand leads to the viral DNA replication being chain-terminated.

Foscarnet (sodium-phosphonoformic acid) is a pyrophosphate analogue which does not require any initial intracellular activation. This active compound directly blocks the pyrophosphate-binding site of the viral DNA polymerase and thereby inhibits the elimination of pyrophosphate from dNTPs.

The above mentioned substances display side-effects which are in some cases substantial. The side-effects of these drugs are summarized in the publication by Crumpacker C S., "Ganciclovir", N. Engl. J. Med. 1996, 335: 721-731).

Thus, administering ganciclovir results, in particular, in a reduction in the number of white blood cells and frequently of the platelets as well. An anaemia can also develop if the drug is administered over a relatively long period. Because of the haematological toxicity, administering the full dose of ganciclovir in combination with other myelotoxic pharmaceuticals can be life-threatening.

Cidofovir exhibits dose-dependent nephrotoxicity. The latter is elicited by a disequilibrium between rapid uptake into the cells of the proximal tubule and a slower efflux into the urine, with this leading to accumulation in the kidneys.

Foscarnet exhibits substantial renal and metabolic toxicity. The nephrotoxicity is based on direct damage to the kidney tubules.

A particularly critical situation with regard to successful therapeutic intervention arises when multiresistance to ganciclovir, foscarnet and cidofovir is manifested in connection with an HCMV infection. The development of resistance is a serious clinical problem and can result in death, particularly in the case of multiresistance. In the pre-HAART (highly active antiretroviral therapy) era, it was essentially AIDS patients with HCMV retinitis who were affected by the development of GCV-resistant strains.

At present, when a ganciclovir-resistant HCMV infection is detected, foscarnet is used as alternative medication. However, a disadvantage of this approach is that a relatively high effective dose of foscarnet is required in order to achieve an efficient antiviral effect. A high effective dose in turn results in toxic side-effects. When a multiresistant HCMV infection develops, no further antiviral agents are available.

A further disadvantage of the virostatic agents which are presently available is their lack of oral bioavailability, which makes it necessary to administer them intravenously. The venous catheters which are inserted for this purpose in connection with continuous therapy can lead to sepsis.

A further problem is the limited diffusion of the highly polar virostatic agents through the blood-brain barrier into the cerebrospinal fluid space. Eckle, et al., "Drug-resistant human cytomegalovirus infection in children after allogenic stem cell transplantation may have different clinical outcomes", *Blood* (2000) 96(9):3286-3289, showed that neither ganciclovir, intravenously or intrathecally, nor foscarnet or cidofovir, were able to have an effect on an HCMV encephalitis which was elicited by a multiresistant HCMV strain following a bone marrow transplantation.

WO 98/38202 discloses lipophilic phosphonoacids/ nucleoside conjugates which exhibit antiviral activity. The compounds disclosed in this document include phosphonoformic acid/nucleoside conjugates, with the conjugates containing at least one lipophilic group and at least one nucleoside group.

SUMMARY OF THE INVENTION

It is an object of the present invention to provide a substance for a method for treating infectious diseases which are elicited by viruses which are pathogenic to humans and which also exhibits high activity in the case of resistant and multiresistant virus strains and can be employed at low doses.

According to the invention, this object is achieved by providing a method for the treatment of viral infections diseases which are elicited by viruses which are pathogenic to humans, comprising administering to a patient an effective amount of an amphiphilic nucleoside-phosphonoformic acid derivative having an esterified or unesterified carboxyl group, preferably a nucleoside-glycerol-(hydroxycarbonyl)-phosphonate, as active compound.

Such nucleoside-phosphonoformic acid derivatives are described in WO 00/34298.

This document discloses the preparation of glyceryl nucleotides which constitute combination preparations and which, on being metabolized, are in each case able to release two active compounds simultaneously. In these glyceryl nucleotides, either two therapeutically active nucleoside derivatives are covalently linked to each other, or one nucleoside derivative is covalently linked to phosphonoformic acid or its salt form (foscarnet), by way of a glycerol lipid backbone.

For example, as active compound, a nucleoside-(5'→2)- 1-O-alkyl-rac-glycerol-3-(hydroxycarbonyl)-phosphonate, with alkyl being a straight-chain or branched saturated or unsaturated radical having more than 6 carbon atoms can be used.

Some of the glyceryl nucleotides described in WO 00/34298 are proposed for treating cancer and infectious diseases. However, the effect of a nucleoside-(5'→2)-1-O-alkyl-rac-glycerol-3-(hydroxycarbonyl)-phosphonate in connection with infectious diseases which are elicited by viruses which are pathogenic to humans is not described.

The nucleoside groups which are to be employed in accordance with the invention are derived from nucleosides and are, in particular, nucleoside groups which do not occur naturally and which comprise a heterocyclic radical which is glycosidically linked to a sugar radical.

3'-Azido-2',3'-dideoxythymidylyl-(5'→2)-1-O-octadecyl-rac-glycerol-3-(hydroxycarbonyl)-phosphonate is, in particular, used as preferred active compound. While this active compound has already been described in WO 00/34298, its effect is not described and nor is its use specifically proposed.

In their own experiments, the inventors were able to demonstrate that 3'-azido-2',3'-dideoxythymidylyl-(5'→2)- 1-O-octadecyl-rac-glycerol-3-(hydroxycarbonyl)-phosphonate (also designated "N3" below) exhibits antiviral activity. The following formula I shows the structure of N3:

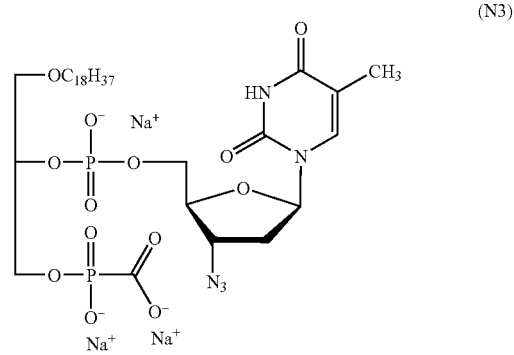

Another object of the invention refers to a method for the treatment of infections diseases which are elicited by retroviruses, in particular by the HI virus, comprising administering to a patient an effective amount of an amphiphilic nucleoside-phosphonoformic acid derivative having an esterified or unesterified carboxyl group, preferably a nucleoside-glycerol-(hydroxycarbonyl)-phosphonate, as active compound.

Because of the immunodeficiency which is elicited by the virus, HIV-infected humans run the particular risk of severe coinfections with viruses which the immune system in healthy people is normally able to control. Advantageously, the use according to the invention of the active compounds can, as a result of the effect of the latter on the HIV virus, prevent consequential infections with other viruses.

In addition, the active compounds can be administered for treating infectious diseases which are elicited by hepatitis B and/or hepatitis C viruses.

In another application, the active compounds can be administered for treating infectious diseases which are elicited by adenoviruses.

Adenoviruses cause a variety of disease syndromes such as infections of the airways, of the eye and of the intestinal tract, which may have severe consequences, in particular in children.

The active compound is furthermore administered for treating infectious diseases which are elicited by human beta and/or gamma herpes viruses, in particular by the Epstein Barr virus and/or the human cytomegalovirus (HCMV).

People who are at a particular risk of developing severe HCMV diseases are HIV-infected patients, in whom the function of the immune system is disturbed. Patients who require medicinal immunosuppression following transplantation of solid organs are likewise at risk, particularly in the first three months. Furthermore, the recipients of bone marrow and stem cell transplants are at high risk of suffering from an HCMV disease until the immune system which has been transferred by the transplantation has become fully functional.

In particular, reinfections with HCMV, or a reactivation, can lead to very severe generalized infections, with a lethal outcome, in patients whose immune system is suppressed. It is therefore advantageous to use the active compounds in AIDS patients suffering from an HCMV infection, for example, since this makes it possible to attack two pathogens simultaneously.

In their own experiments, the inventors were also able to demonstrate that an active compound used in accordance with the invention exhibited an antiviral activity towards ganciclovir-sensitive HCMV strains which was comparable with that of ganciclovir.

In addition, this active compound proves to be highly active towards ganciclovir-resistant CMV strains.

This is particularly advantageous in the case of an infection with HCMV strains which are resistant to GCV since, in this instance too, it is not necessary to use a dose of the active compound which is any larger than that used in the case of GCV-sensitive HCMV strains.

In further experiments, the active compound possessed an antiviral activity which was approx. 40 times higher than that of foscarnet, even against ganciclovir-resistant HCMV strains.

This is particularly advantageous since, while it has previously been possible to use foscarnet to exert an effect on the replication of ganciclovir-resistant HCMV strains in vitro and in vivo, it has not been possible to do this using a molar concentration as low as that used when using N3. In this instance, it is particularly advantageous that this makes it possible to reduce the severe side-effects, in particular the nephrotoxicity, which are elicited by the long-term administration of foscarnet.

It is furthermore advantageous, when using nucleoside-phosphonoformic acid derivatives for the manufacture of medicaments, that the additive myelotoxic effect of ganciclovir and azidothymidine, and the limited treatment possibilities which result therefrom, can be overcome.

In another application, the active compound is administered for diseases which are elicited by multiresistant HCMV strains.

For example, Eckle, et al., Drug-resistant human cytomegalovirus infection in children after allogenic stem cell transplantation may have different clinical outcomes, *Blood* (2000) 96(9):3286-3289, describe an HCMV strain which has developed multiresistance to ganciclovir, foscarnet and cidovir.

Since it has not previously been possible to find any active compound which is directed against multiresistant HCMV strains and which has a lower toxicity, but the same activity, as foscarnet, for example, the nucleoside-phosphonoformic acid derivatives constitute extremely effective substances for controlling multiresistant HCMV strains.

Nucleoside-phosphonoformic acid derivatives can be used for diseases, such as pneumonia, hepatitis, colitis, retinitis and encephalitis, which are elicited by HCMV. The diseases are very dangerous for immunosuppressed patients, in particular.

For example, a pharmaceutical comprising the active compound is administered parenterally and/or orally.

In this connection, the active compound can be administered together with one or more pharmaceutically acceptable excipients.

In this connection, "excipients" or auxiliary substances are understood as being those substances which are customarily used, in producing pharmaceuticals, as diluents, binders, suspending agents, lubricants, stabilizers, etc., either as solution or as solid substance. Examples include, but are not limited to this, water, salt solutions, alcohols, vegetable oils, polyethylene glycols, gelatine, lactose, glucose, amylose, cellulose, glycerol, magnesium stearate, albumin, monoglycerides, diglycerides, polyvinylpyrrolidone, etc. A number of other suitable substances can be found in A. Kibbe, Handbook of pharmaceutical excipients, 3rd ed., 2000, American Pharmaceutical Association and Pharmaceutical Press.

The pharmaceutical preparation can, if desired, be sterilized and can additionally comprise preservatives, stabilizers and/or dispersants, emulsifiers, buffers, dyes, flavourings, etc., which do not interfere with the active compound.

Oral administrations can be present in the form, for example, of tablets, capsules or lozenges, or as liquid preparations in the form of a syrup, with these administrations being produced in accordance with known methods, for example while adding carbohydrate binders, such as maize starch, etc. For a parenteral administration, known methods can likewise be used to formulate the substance as an injection or infusion.

In this connection, the active compound can also be incorporated for example into liposomes and/or nanoparticles, with the lipophilic radicals which are in each case introduced having a major influence on the size and stability of the liposomes.

In addition to this, the active compound can also be administered in combination with other active compounds or pharmaceuticals, such as reverse transcriptase inhibitors, protease inhibitors, interferon or interleukin II, in a therapeutic application, or in connection with immunomodulating therapies such as bone marrow or stem cell transplantations/transplantations of solid organs, or together with active compounds which increase the number of lymphocytes. It is also possible to use several nucleoside-phosphonoformic acid derivatives simultaneously in one formulation.

In this context, the precise dose depends on the way of administration, the condition to be treated, the severity of the disease, the weight and age of the patient to be treated, etc.

It will be understood that the features described above and those which are still to be explained below can be used not only in the combination which is in each case specified but also in other combinations, or on their own, without departing from the scope of the present invention.

Other advantages ensue from the examples.

EXAMPLES

Preparing Esterified and Unesterified 3'-azido-2',3'-dideoxythymidylyl-(5'→2)-1-O-octadecyl-rac-glycerol-3-(hydroxycarbonyl)-phosphonate Based on the synthesis described in WO 00/34298, 3'-azido-2',3'-dideoxythymidylyl-(5'→2)-1-O-octadecyl-rac-glycerol-3-(hydroxycarbonyl)-phosphonate (N3 in that which follows) was prepared in three steps:

1st Step:

15.8 g (23 mmol) of 3-O-(4-monomethoxytrityl)-1-O-octadecyl-rac-glycerol-2-hydrogen phosphonate were dissolved, together with 8 g (30 mmol) of 3'-azido-2',3'-dideoxythymidine, in 70 ml of anhydrous pyridine. The solution was then cooled down to 10° C. after which 18 ml (148 mmol) of pivaloyl chloride were added while excluding moisture and the whole was stirred at room temperature for 7 min. The mixture, which was then cooled down to 0° C., was treated with 18 ml of water and 105 ml of a 0.2 M solution of iodine in THF and stirred for 1 h without being cooled. The excess iodine was removed by adding solid sodium hydrogen sulphite before the reaction mixture was concentrated down to a syrup in a rotary evaporator. The syrup was taken up in 150 ml of chloroform and extracted by shaking three times with 450 ml of a water/methanol/ $NaCl_{saturated}$ 1:2:1 (v/v/v) mixture. The organic phase was once again concentrated down to a syrup, which was then coevaporated three times with in each case 200 ml of toluene. In order to replace the 4-monomethoxytrityl group with hydrogen, the syrup was dissolved in 150 ml of acetic acid/water 4:1 (v/v) after which this solution was heated to 50° C. for 15 min and then once again concentrated down to a syrup in a rotary evaporator. The acetic acid was removed by coevaporating with toluene under an oil pump vacuum and the syrup which was obtained in this connection was then dissolved in 100 ml of chloroform/methanol (95:5) (v/v) and chromatographically purified on a silica gel column using a chloroform/methanol gradient. After the solvent had been evaporated from the combined product-containing fractions on a rotary evaporator, there then remained a solid, which was recrystallized from methanol at −25° C., resulting in 10.5 g (15.6 mmol) of 3'-azido-2', 3'-dideoxythymidylyl-(5'→2)-1-O-octadecyl-rac-glycerol being obtained as the precursor of the active compound. On a silica gel thin layer plate, this precursor had an $R_f$ value of 0.5 in the solvent system chloroform/methanol 7:3 (v/v).

2nd Step:

2.3 g (12 mmol) of (ethoxycarbonyl)phosphorous acid dichloride were dissolved in 30 ml of trimethyl phosphate and the solution was cooled down to approx. 0° C. in an ice bath while being stirred. 4.0 g (6 mmol) of 3'-azido-2',3'-dideoxythymidylyl-(5'→2)-1-O-octadecyl-rac-glycerol were then added, while stirring, after which the mixture was stirred, while excluding moisture, firstly in the ice bath (0° C.) for a further 5 h and then at room temperature overnight. The reaction mixture was then dissolved in 120 ml of diethyl ether and this solution was extracted by shaking twice with in each case 100 ml of $H_2O$. The acidic aqueous phase was adjusted to pH 6.5 with 2 M sodium hydroxide solution in the ice bath, after which it was concentrated and the residue was coevaporated once with toluene. The residue was then suspended in 100 ml of diethyl ether and this suspension was kept at 4° C. for crystallization. The resulting precipitate was extracted by suction, washed with cold diethyl ether and dried. The mother liquor was concentrated down to approx. ⅓ of the initial volume for the postprecipitation, and the precipitate now obtained was worked up in an analogous manner. The combined precipitates (crude product) were dissolved in 0.05 M ammonium acetate/methanol (2:8) (v/v) and chromatographically purified on a reversed phase ($RP_{18}$ column) in an ammonium acetate/methanol gradient. The combined product-containing fractions were concentrated down to approx. ¼ of the initial volume and then lyophilized. 3.2 g of ethyl 3'-azido-2',3'-dideoxythymidylyl-(5'→2)-1-O-octadecyl-rac-glycerol-3-(hydroxycarbonyl)-phosphonate are obtained. The product is the esterified form of N3 and is, in the following, designated N4.

3rd Step:

2 g of ethyl 3'-azido-2',3'-dideoxythymidylyl-(5'→2)-1-O-octadecyl-rac-glycerol-3-(hydroxycarbonyl)-phosphonate (N4) were dissolved in 50 ml of water after which 107 ml of 1 M sodium hydroxide solution were added; after this mixture had been stirred at room temperature for 10 min, it was neutralized to pH 7 with a cation exchanger. This solution, which had been extracted by suction, was adjusted to pH 7.5 to 8 with sodium hydroxide solution and then lyophilized. The lyophilisate was chromatographically purified on a reversed phase ($RP_{18}$) column in an ammonium acetate/methanol gradient and yielded 1.5 g of 3'-azido-2', 3'-dideoxythymidylyl-(5'→2)-1-O-octadecyl-rac-glycerol-3-(hydroxycarbonyl)-phosphonate (N3) in the form of a colourless powder which, on a silica gel thin layer plate, had an $R_f$ value of 0.1 in the solvent system chloroform/methanol 6:4 (v/v).

Demonstrating the HCMV-Specific Antiviral Activity

A modified cell-adapted plaque reduction assay was carried out for demonstrating the HCMV-specific antiviral activity of N3. Cocultures of infected and uninfected human foreskin fibroblasts (HFFs) were used for this purpose.

The implementation of the assay was described for the first time in Prix, et al., "A simplified assay for screening of drug resistance of cell-associated cytomegalovirus strains," *Journal of Clinical Virology* (1998) 11:29-37, and Prix, et al., "Comprehensive restriction analysis of the UL97 region allows early detection of ganciclovir-resistant human cytomegalovirus in an immunocompromised child," *Journal of Infectious Diseases* (1999) 180:491-495, and is briefly described below.

Preparing the HFF Cells

HCMV primary isolates on HFF cells in tube culture were passaged on subconfluent monolayers of HFF grown in small cell culture flasks (25 $cm^2$), and cultured. When an approx. 20-40% cytopathic effect (CPE) had been reached, the cells were washed with phosphate-buffered saline (PBS) and the monolayer was removed by trypsinization. After the trypsin had been inactivated, the pellet was taken up in Eagle's minimal essential medium (MEM)-10% FCS (foetal calf serum) and subjected to mild filtration for the purpose of separating off cell aggregates.

In parallel, uninfected HFF cells were cultured on 175 $cm^2$ dishes, washed, trypsinized and, after further purification steps, taken up in MEM-10% FCS.

Preparing the Cocultures

In order to prepare cocultures, the infected cells were mixed with the uninfected cells in the following manner: $2.5 \times 10^4$ uninfected cells/100 μl were mixed, in two different ratios, with 500 and 1000 infected cells/100 μl. In each case 100 μl of each of these dilution steps were pipetted in triplicate into a 96-well microtitre plate. In order to ensure that the cells adhered to the microtitre plate bottom, the cocultures were incubated for at least 4 h before the medium was carefully removed.

Loading the Virostatic Agents

Immediately after the medium had been removed, the virostatic MEM solutions, which have already been previously prepared and which contain increasing concentrations of ganciclovir (GCV), foscarnet (PFA) or 3'-azido-2',3'-dideoxythymidylyl-(5'→2)-1-O-octadecyl-rac-glycerol-3-(hydroxycarbonyl)-phosphonate (in the following: N3), were loaded onto the microtitre plate with of 200 μl per well.

The cultures were then incubated for 4 days so as to enable the viruses from the infected single cells to spread in the form of plaque formation by infecting the neighbouring cells.

Detecting HCMV by Means of In Situ ELISA

Following the 4-day incubation, the medium was carefully poured off and the microcultures were permeabilized, and fixed, with 200 µl of ice-cold (−20° C.) methanol. After 20 min, the methanol was removed and the cells were washed twice with PBS.

The primary antibody (anti-IE1-pp72, E13 clone, Paesel & Lorei, Germany), which is directed against the HCMV immediate early antigen (UL123) of HCMV, was then added. After the plate had been incubated for 1 h, the cells were washed and incubated for 1 h with the secondary antibody (horseradish peroxidase-conjugated mouse HCMV IgG antibody; DAKO, Denmark). After the peroxidase/ $H_2O_2$ substrate had been added, the HCMV immediate early antigen was detected, under a microscope, in the nuclei of the infected fibroblasts as a result of the in situ brown staining. The result was recorded photographically in selected examples.

The concentrations 0 and 5 µM (measurement series 0 to 50 µM) were recorded in the case of GCV while the concentrations 0 and 300 µM (150-500 µM) were recorded in the case of PFA and 6.25 µM (3-50 µM) was recorded in the case of N3. 6.25 µM of the structurally identical, ethyl-esterified compound N4 were also included.

RESULTS

GCV-Resistant and PFA/CDV-Sensitive HCMV Strains

In this experiment, 500 HCMV-infected HFF cells/microculture were used. As compared with 5 µM GCV, 6.25 µM N3 produced a strong plaque reduction. Comparison of the average plaque numbers/microculture (GCV: 19.5; N3: 5.7) also showed that the compound N3 reduced both the number of the plaques and their size extremely effectively (results not shown).

While a comparison of the effects of N3 and PFA on plaque reduction clearly showed that both PFA (number of plaques: 5) and N3 (7.5) markedly reduced plaque number and size as compared with the negative control containing 0 µM PFA (37.9), a considerably higher concentration of PFA had to be used in order to achieve an activity which was comparable to that of N3 (300 µM PFA compared with 6.25 µM N3).

Multiresistant HCMV Strain

The HCMV strain employed was GCV/PFA/CDV-resistant (=multiresistant HCMV strain, see Eckle, et al., "Drug-resistant human cytomegalovirus infection in children after allogenic stem cell transplantation may have different clinical outcomes," *Blood* (2000) 96(9):3286-3289). For the coculture in this case, 1500 HCMV-infected HFF cells/microculture were used.

Comparing the average plaque numbers made it clear that N3 is highly active against the multiresistant HCMV strain (20.5 in the case of PFA as compared with 2.3 in the case of N3).

Evaluation

For correctly evaluating the plates, the norm was applied that a plaque had to consist of a group of cells containing at least 10 individual cells in order to be included in the count. The $ID_{50}$ values, based on the average plaque number, were calculated by nonlinear regression analysis using probit analysis (statistical software package, SPSS, Munich), with the concentration of the compound which is required to reduce the number of plaques by 50% ($ID_{50}$ values) being determined.

In a preliminary screening, it was found that a nucleoside-(5'→2)-1-O-octadecyl-rac-glycerol-3-(hydroxycarbonyl)-phosphonate exhibited a markedly reduced antiviral effect in vitro when the hydroxycarbonylphosphonate group was esterified (=N4).

Table 1 below shows the summarized results, which were obtained from determining the $ID_{50}$ values as well as the 95% confidence interval, of the test series which are in each case indicated in regard to a GCV-sensitive HCMV strain (column 1) and in regard to a GCV-resistant HCMV strain (column 2) as far as using GCV and N3 is concerned.

TABLE 1

| | Antiviral activity of N3 as compared with GCV | | | |
|---|---|---|---|---|
| Substance | $ID_{50}$ (95% CI): µM ($GCV_{sens}/PFA_{sens}/CDV_{sens}$) $N_{iz}$ = 500/microculture | | $ID_{50}$ (95% CI): µM ($GCV_{res}/PFA_{sens}/CDV_{sens}$) $N_{iz}$ = 1000/microculture | |
| GCV | 2.8 (1.5-4.4) | 1.96 (0.2-4.1) | 14.3 (12.0-76.0) | 13.6 (4.5-72.6) |
| N3 | 4.0 (2.3-6.2) | | 1.3 (0.5-2.2) | 2.2 (0.9-3.5) |

As can be seen from column 1 in the table, N3 exhibits an antiviral activity which is comparable to that of GCV in the case of a GCV/PFA/CDV-sensitive HCMV strain (2.8 µM in the case of GCV as compared with 4.0 µM). In each case 500 infected cells were employed/microculture in this instance.

N3 is highly active against the GCV-resistant HCMV strain, resulting in an $ID_{50}$ which is approx. 11× lower than that for GCV (14.3 in the case of GCV as compared with 1.3 in the case of N3), with 1000 infected cells/microculture being used in this instance.

Table 2 below summarizes the $ID_{50}$ values, and the 95% confidence interval, which were obtained from N3, as compared with PFA itself, in regard to a GCV-resistant HCMV strain.

TABLE 2

| | Antiviral activity of N3, as compared with PFA, against a GCV-resistant HCMV strain | |
|---|---|---|
| Substance | $ID_{50}$ (95% CI): µM ($GCV_{res}/PFA_{sens}/CDV_{sens}$) $N_{iz}$ = 1000/microculture | |
| PFA | 68.8 (10.4-111.4) | 62.9 (43.2-81.1) |
| N3 | 1.8 (0.5-3.2) | 1.6 (0.5-2.9) |

The results summarized in Table 2 (multiple determinations) show that N3 possesses an antiviral activity against a GCV-resistant/PFA-sensitive HCMV strain which is approx. 40× higher than that of PFA itself (64.8 in the case of PFA as compared with 1.8 in the case of N3). This means that a markedly lower quantity of active compound had to be used in the case of N3, as compared with PFA itself, for achieving antiviral activity. 1000 infected HFF cells/microculture were used.

Table 3 below shows the results for the $ID_{50}$ values and the 95% confidence intervals for N3, as compared with PFA, in regard to a multiresistant HCMV strain, i.e., a GCV-, PFA- and CDV-resistant strain.

TABLE 3

Antiviral activity of N3, as compared with PFA, against a multiresistant HCMV strain

| Substance | $ID_{50}$ (95% CI): μM Multiresistant: $GCV_{res}/PFA_{res}/CDV_{res}$ $N_{iz}$ = 1500/microculture | | |
|---|---|---|---|
| PFA | 309.7 (239.9-394.4) | 336.5 (294.8-390) | 474.1 (319-1098) |
| N3 | 4.0 (1.2-6.8) | 6.5 (5.1-7.8) | 2.4 (1.0-3.2) |
| $ID_{50PFA}/ID_{50N3}$ | 77.4 | 51.8 | 197.5 |

Table 3 shows the results of three experimental series. They show N3 is highly active against a multiresistant HCMV strain, with this being expressed in a markedly lower $ID_{50}$ value for N3 as compared with PFA and, as a result, in a high $ID_{50PFA}/ID_{50N3}$ ratio ($ID_{50PFA}/ID_{50N3}$: 50-200). 1500 infected cells/microculture were used.

In summary, the inventors were consequently able to demonstrate that, because of its high activity, N3 is an extremely effective alternative to ganciclovir, foscarnet and cidovir when treating viral infectious diseases. A compound whose hydroxycarbonylphosphonate group was esterified with ethyl (=N4), but which was otherwise structurally identical to N3, did not exhibit any antiviral activity against multiresistant strains. In addition to this, because of its high antiviral activity even at low doses, N3 is to be preferred to the substance PFA in the case of partially resistant viruses since using N3 makes it possible to avoid the high nephrotoxicity of PFA which is exhibited, in particular, when high doses are given continuously.

The inventors were furthermore able to demonstrate that the substance N3 exhibited antiviral activity in the case of multiresistant HCMV strains and that use of the substance consequently offers a unique treatment option in the case of diseases which are elicited by multiresistant virus strains.

Since N3 was determined to have a cytotoxic effect in vitro towards human prepuce fibroblasts only at concentrations of >125 μM, adequate therapeutic breadth for in vivo use consequently also exists.

The invention claimed is:

1. A method for treating infectious diseases which are elicited by human cytomegalovirus strains, said method comprising administering an effective amount of 3'-azido-2',3'-dideoxythymidylyl-(5'→2)-1-O-octadecyl-rac-glycerol-3-(hydroxycarbonyl)-phosphonate.

2. The method of claim 1, wherein the substance is administered for treating infectious diseases which are elicited by ganciclovir-sensitive human cytomegalovirus strains.

3. The method of claim 1, wherein the substance is administered for treating infectious diseases which are elicited by ganciclovir-resistant human cytomegalovirus strains.

4. The method of claim 1, wherein the substance is administered for treating infectious diseases which are elicited by multiresistant HCMV strains.

5. The method of claim 1, wherein the medicament is administered parenterally.

6. The method of claim 1, wherein the medicament is administered orally.

* * * * *